United States Patent
Kuperberg et al.

(10) Patent No.: US 10,874,775 B2
(45) Date of Patent: Dec. 29, 2020

(54) METHOD AND APPARATUS FOR A STENT WITH A CAPPED-RELEASE MECHANISM (CRM)

(71) Applicants: Stephen Kuperberg, New york, NY (US); Yitzhak Rosen, Highland Park, NJ (US)

(72) Inventors: Stephen Kuperberg, New york, NY (US); Yitzhak Rosen, Highland Park, NJ (US)

( * ) Notice: Subject to any disclaimer, the term of this patent is extended or adjusted under 35 U.S.C. 154(b) by 235 days.

(21) Appl. No.: 15/946,351

(22) Filed: Apr. 5, 2018

(65) Prior Publication Data

US 2019/0307930 A1  Oct. 10, 2019

(51) Int. Cl.
| A61L 33/00 | (2006.01) |
| A61L 31/16 | (2006.01) |
| A61L 31/14 | (2006.01) |
| A61F 2/89 | (2013.01) |

(52) U.S. Cl.
CPC ............ *A61L 33/0011* (2013.01); *A61F 2/89* (2013.01); *A61L 31/148* (2013.01); *A61L 31/16* (2013.01); *A61F 2210/0004* (2013.01); *A61F 2220/0091* (2013.01); *A61F 2250/0068* (2013.01); *A61L 2300/42* (2013.01); *A61L 2400/18* (2013.01)

(58) Field of Classification Search
CPC ...... A61F 2/06; A61F 2/82; A61F 2250/0067; A61L 31/16; A61L 33/0011
See application file for complete search history.

(56) References Cited

U.S. PATENT DOCUMENTS

| 6,620,194 | B2 | 9/2003 | Ding et al. |
| 7,901,703 | B2 | 3/2011 | Hossainy |
| 2007/0142898 | A1* | 6/2007 | Sirhan et al. ............. A61F 2/06 |
| 2007/0254012 | A1 | 11/2007 | Ludwig et al. |
| 2009/0053392 | A1* | 2/2009 | Kramer-Brown et al. .................. A61F 2/06 |
| 2014/0155825 | A1 | 6/2014 | Scheller et al. |
| 2015/0094641 | A1* | 4/2015 | Park et al. .......... A61F 9/00781 |
| 2019/0008995 | A1* | 1/2019 | Roth ..................... A61L 27/047 |

OTHER PUBLICATIONS

Ost, David, Gould MK, "Decision making in patients with pulmonary nodules," American journal of respiratory and critical care medicine vol. 185,4 (2012).

* cited by examiner

*Primary Examiner* — Jason-Dennis N Stewart
(74) *Attorney, Agent, or Firm* — Patent Ventures, LLC

(57) ABSTRACT

Disclosed and claimed is any one of long-dwelling body lumen apparatus, such as a catheter or stent (c/s), said c/s comprising: at least one lumen fittingly disposed within a tubular member; a scaffold circumferentially disposed around at least one of an outer surface of at least the tubular member; said scaffold radially extending for at least a portion of the length of the at least tubular member. Furthermore, the scaffold comprised of any one of a pattern of interlocking struts with individual well-like reservoirs disposed; each reservoir having a depth sufficient enough to house at least a first agent of any one of a chemical moiety, each of the reservoirs capped to form an enclosure; and wherein a delayed degradation of said cap results in a sudden release of the housed at least first agent. Any number of agents, reservoirs, and cap configurations may be possible.

21 Claims, 8 Drawing Sheets

METHOD AND APPARATUS FOR A STENT WITH A CAPPED-RELEASE MECHANISM (CRM)

BACKGROUND OF THE INVENTION

Field of Invention

The field of the invention relates to a stent or catheter scaffold pre-attached or attachable with a capped-release of at least one agent, more particularly, a time-controlled and zoned-release of agents to disrupt the granulation tissue or fibrin sheath that forms abluminal or mucus build-up that forms luminal.

Related Art

Long term stent or catheter (s/c) applications facilitate care for patients with chronic illness by providing easy venous or airway access for laboratory tests, delivering therapeutic payloads, etc. However, (s/c) occlusions or thrombosis is a pervasive issue during the administration of long-term s/c applications. Fibrin sheath formation is among the most common contributing factors for s/c occlusions. The incidence of central venous fibrin sheath formation is reported to occur in 42%-100% of central venous catheters. Fibrin sheath are a heterogeneous matrix of cells and debris that form around s/c, and in particular, encase the outer wall and the end-holes of the s/c, leading to port dysfunction leading to difficulty in aspiration and/or a high resistance to the injection of fluids.

In the instance of partial occlusion, the ebb-and-flow of fluids may affect the flow rate and efficacy of therapy. Worse yet, there are a variety of complications that may arise from even partial encasement, including sepsis, extravasation of infusions, and venous thrombosis, just to name a few. Extravasation of fluids or intravenous medication is a less common, but certainly significant complication that can result in tissue loss and necrosis. Thrombus that forms on the fibrin sheath or the fibrin sheath itself can, on rare occasion, become dislodged and embolize to the pulmonary circulation. Finally, there have been reports that the presence of the sheath is a risk factor for c/s-related bacteremia and infection. Moreover, there are a number of additional complications that may be related to the treatment of occluded c/s, including intracranial hemorrhage (ICH), major bleeding (MB), and embolism.

Granulation tissue or fibrin sheath may not form for at least a month after placement of the c/s. In the case of pulmonary stents, there are three main types of pulmonary stents: silicone, metal, or hybrid. Each type has advantages and disadvantages. The common denominator is that they are all prone to a build of granular tissue or fibrin sheath on either open ends of the stent within a month of placement. The global delivery of a fast-acting agent loses efficacy as a disruptive agent by the time the granular tissue has formed with delay—not to mention the fact that it isn't localized depending on build-up propensity. Drug-eluting stents with delayed release of agents result in a slow release of agent, rather than a controlled-release, which refers to an immediate release of a completely intact agent upon a controlled-delay. Contrastingly, the slow release approach deployed by most extant drug-eluting stents, still results in a release of an agent with a loss of efficacy by the one-month mark of stent dwelling. The inclusion of pulmonary stent coverings, likewise, do not address the issue of the slow release or global administration.

Self-expanding or migrating pulmonary stents have been shown to have higher incidence rates of granulation. According to a recent peer-reviewed study published in Chest (Ost, et al., 2012), it is believed that the differences in granulation are attributed to motion-mediated trauma during the dwelling phase. The trauma led from either repetitive stent motion of migrating stents or stent-expansion attributes to the higher incidence rates of granulation tissue formation. Moreover, according to the same study, the median time to granulation is 1.4 months, versus 5-7 days of hemodialysis catheter dwelling. As a result, any solution featuring global and immediate delivery of granulation tissue disrupting agents or mechanical ablation is not efficacious. The pharmacokinetic features of the coated or eluted drug are not aligned with the delayed formation of granulation tissue in metal, silicon, or hybrid stents. The drug release from a Placitaxel-eluting stent is typically 70% or more before the first month of placement (Wang, et al., Chin. Med. J. 2016), well before the median onset of granulation tissue (Ost, et al., 2012). Common adverse reactions to a build up or accumulation of Placitaxel is inflammation, adverse drug interactions, incomplete stent apposition, or increased in-stent thrombosis rates.

Ludwig et. al. (Ser. No. 11/413,404) discloses a stent with a plurality of particles being releasably embedded within any one of an abluminal layer, inner layer, or luminal layer, the particles being configured to be released from any one of the layers due to erosion of any one of the layers. However, the stent layers described in Ludwig are the standard axial segments of any traditional stent scaffolding that is widely known in the art; with the addition of a layer degradation and active agent release aspect. Ludwig does not disclose for a unique configuration of agent enclosures with differential degradation rates, thereby control-releasing an anti-granulation tissue agent during peak granulation tissue build-up. Ludwig simply does not address the specific problem of granulation tissue build-up or the attendant issue of a delayed onset of granulation tissue build-up. Moreover, studies have shown that the release of embedded agents by a slow erosion of the embedded layer that radially extends the length of the stent results in an increase of inflammation and other unfavorable outcomes. What's more, the release of the embedded agent is slow and pegged to the degradation rates of the embedded layer, and not a sudden release of an agent housed within a capped enclosure with a delayed degradation. Extant stents do not provide for a sudden release of a housed anti-granulation agent upon a timed-delay. Furthermore, extant stents do not provide for a unique embedding configuration of various agent enclosures with differential rates of degradation to combat varying granulation tissue or mucus build-up in at least one of luminal surface, abluminal surface, distal and proximal openings.

None of these solutions involve stents or stent sleeves/coverings with a reservoir cap situated anterior on a longitudinal-plane above a reservoir; a cap with a degradation rate tuned to a controlled delay based on the zonal/surface location of the reservoir; a cap configured for sudden-release of a housed (not embedded) agent to disrupt or prevent local recurrence of delayed onset granulation tissue. Furthermore, the cap with varying configurations and compositions to confer varying degradation rates, will additionally provide better local fixation with drugs and/or materials to induce local desired reactions. There is a void in the market and art for stents with time-delayed, yet sudden release of housed anti-granulation agents in a stent environment to react to delayed onset granulation tissue. There is, additionally, a void in the market and art for stents with zone-specific degradation/elution.

SUMMARY

The present invention fills a void left behind by the currently existing c/s solutions and references. The present invention provides for an apparatus and method for a capped-release of agents: controlled, yet sudden release of an anti-granulation agent housed in a cap enclosure on at least one of the luminal, abluminal, and proximal or distal openings of the stent. Capped release referring to the controlled degradation of the cap, resulting in a sudden release of anti-granulation agents. The controlled degradation and sudden release mechanism results in a released agent with a higher therapeutic payload, in which caps are tuned with degradation rates depending on the zone and surface in which they will be embedded.

In one aspect of the invention, a stent apparatus may comprise: at least one lumen fittingly disposed within a tubular member; a scaffold circumferentially disposed around at least one of an outer and, or inner surface of at least one of the tubular member; said scaffold radially extending for at least a portion of the length of the tubular member; said scaffold comprised of any one of a pattern of struts with an individual well depth sufficient enough to be house a first agent of any one of a chemical moiety with a capped enclosure. Furthermore, a delayed degradation of said cap resulting in a sudden release of the housed first agent; and said first agent effectuating a prevention of a local recurrence of a tumor, granulation tissue, or fibrin sheath.

In another aspect of the invention, a stent sleeve may comprise: at least one sleeve configured to be fittingly disposed over a tubular member portion of a stent; a scaffold circumferentially disposed around at least one of an outer surface of at the sleeve; said scaffold radially extending for at least a portion of the length of the sleeve; said scaffold comprised of any one of a pattern of struts with an individual well disposed therebetween, each well with a depth sufficient enough to be house a first agent of any one of a chemical moiety with a capped enclosure. Furthermore, a delayed degradation of said cap resulting in a sudden release of the housed first agent; and said first agent effectuating a prevention of a local recurrence of a tumor or granulation tissue.

In yet another aspect, the cap may have any one of a configuration, such as a flat, concave, or steeple configuration. Further, the cap may be of any one of a bioabsorbal, bioresorbal, or biodegradable composition. Each specific configuration and composition may confer a different degradation rate of the cap, thereby releasing the anti-granulation agent suddenly after the timed degradation of the cap. Various applications may call for varying rates of degradation and sudden release of anti-granulation agents depending on the dwelled environment.

In yet another aspect, wells proximal to port openings may have a higher payload and, or the cap on wells proximal to port openings may have a faster degradation rate—in order to account for the port openings propensity for granulation tissue build up. The perimeter edge of cap openings may additionally have an edge reinforcement to further combat edge build-up of at least one of granulation tissue, fibrin tissue, mucus, and any secretory incrustation.

In yet another aspect, the apparatus may enable a staged luminal release of anti-mucosals, the apparatus comprising: a first anti mucosal layer coating on a luminal surface of a stent; a first bioabsorbal layer with a specific degradation rate coupled to the first anti mucosal layer; at least one other anti-mucosal layer coupled to the first bioabsorbal layer; at least one other bioabsorbal layer with a different degradation rate from the first bioabsorbal layer and coupled to the at least one other anti-mucosal layer and exposed to a stent lumen; and wherein the at least one other bioabsorbal layer degrades immediately upon stenting to release the at least one other anti-mucosal layer immediately as a prophylactic, and a delayed degradation of the first bioabsorbal layer resulting in a delayed release of the first anti-mucosal layer as a booster anti-mucosal response.

In yet another aspect, the luminal surface of a stent may have just one bioabsorbal layer, the immediate degradation of which exposes the one anti-mucosal. The luminal surface of the stent may also have a bioabsorbal layer embedded with an anti-mucosal agent—rather than degrading and exposing an anti-mucosal layer. Whether the luminal surface is configured with a single or multi-absorbal layer, the abluminal surface may concurrently be disposed with the capped enclosures for capped-release of the anti-granulation agents. Capped release referring to the controlled degradation of the cap, resulting in a sudden release of anti-granulation agents.

Aspects and advantages of this invention may be realized in other applications, aside from the intended application. Other applications may include c/s for any one of a pulmonary, cardiac, vascular, and urological environment. Any one of a device intended for prolonged dwelling in any one of a body lumen may take advantage of the claimed invention: Stents or in-dwelling catheters (whether vascular, non-vascular, urinary, etc.); any tubular or non-tubular devices; any valves, prosthesis, nails, or orthopedic devices; any leads, wires, pumps, or sensors, which come into contact with any tissue or organ.

Other aspects and advantages of the invention will be apparent from the following description and the appended claims. It is to be understood that the foregoing general description and the following detailed description are exemplary and explanatory only, and are not necessarily restrictive of the disclosure. The accompanying drawings, which are incorporated in and constitute a part of the specification, illustrate subject matter of the disclosure and together with the general description, serve to explain the principles of the present disclosure. The disclosure will be understood by those skilled in the art from the following detailed description and drawings.

BRIEF DESCRIPTION OF DRAWINGS

The drawings illustrate the design and utility of embodiments of the present invention, in which similar elements are referred to by common reference numerals. In order to better appreciate the advantages and objects of the embodiments of the present invention, reference should be made to the accompanying drawings that illustrate these embodiments. However, the drawings depict only some embodiments of the invention, and should not be taken as limiting its scope. With this caveat, embodiments of the invention will be described and explained with additional specificity and detail through the use of the accompanying drawings in which.

DETAILED DESCRIPTION OF DRAWINGS

Figure 1:
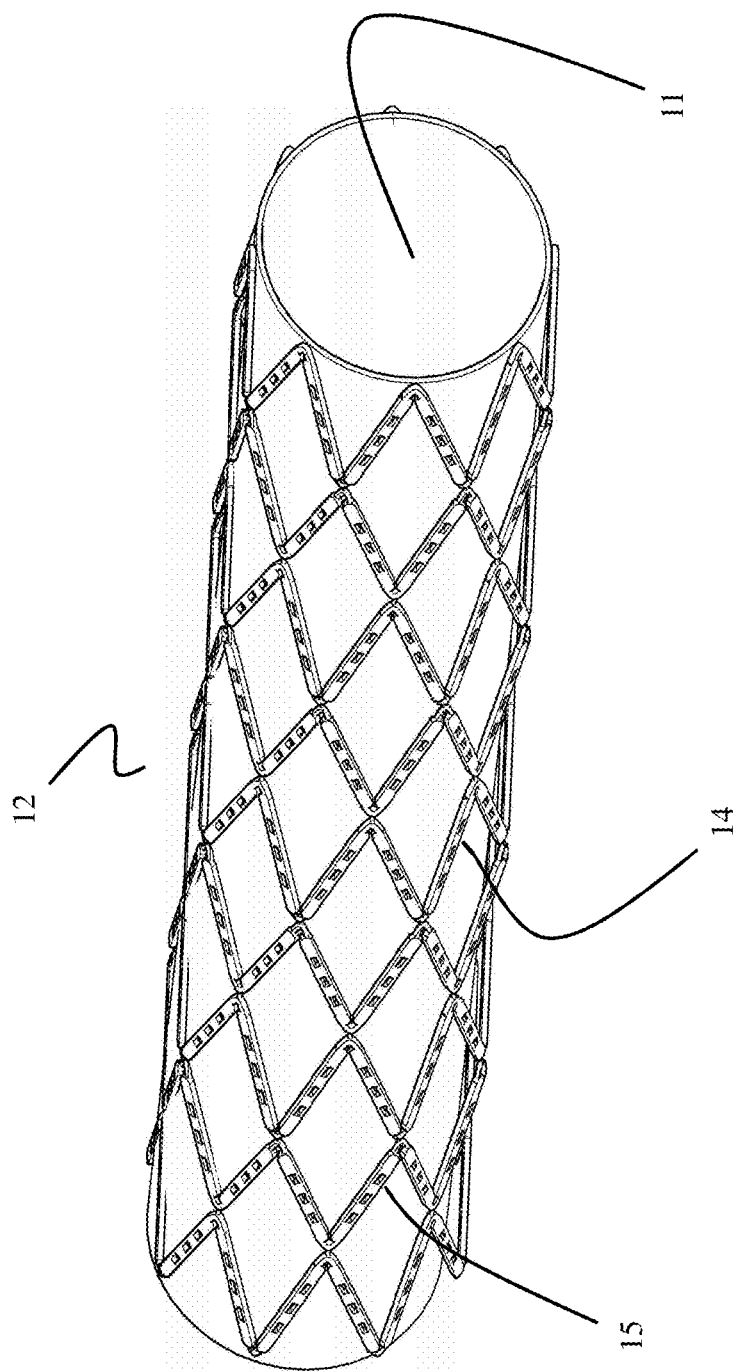
FIG. 1 is a top perspective of the stent according to an aspect of the invention.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Embodiments of the invention are described herein with reference to cross-section illustrations that are schematic illustrations of idealized embodiments (and intermediate structures) of the invention. As such, variations from the shapes of the illustrations as a result, for example, of manufacturing techniques and/or tolerances, are to be expected. Thus, embodiments of the invention should not be construed as limited to the particular shapes of regions illustrated herein but are to include deviations in shapes that result, for example, from manufacturing. Thus, the regions illustrated in the figures are schematic in nature and their shapes are not intended to illustrate the actual shape of a region of a device and are not intended to limit the scope of the invention.

Unless otherwise defined, all terms used in disclosing embodiments of the invention, including technical and scientific terms, have the same meaning as commonly understood by one of ordinary skill in the art to which this invention belongs, and are not necessarily limited to the specific definitions known at the time of the present invention being described. Accordingly, these terms can include equivalent terms that are created after such time. It will be further understood that terms, such as those defined in commonly used dictionaries, should be interpreted as having a meaning that is consistent with their meaning in the present specification and in the context of the relevant art and will not be interpreted in an idealized or overly formal sense unless expressly so defined herein. All publications, patent applications, patents, and other references mentioned herein are incorporated by reference in their entirety.

It will be understood that when a layer is referred to as being "on top of" another layer, it can be directly on the other layer or intervening layers may also be present. In contrast, when a layer is referred to as "contacting" another layer, there are no intervening layers present. Similarly, it will be understood that when a layer is referred to as being "below" another layer, it can be directly under the other layer or intervening layers may also be present.

It will also be understood that, although the terms first, second, etc. may be used herein to describe various elements, these elements should not be limited by these terms. These terms are only used to distinguish one element from another. For example, a first layer could be termed a second layer, and, similarly, a second layer could be termed a first layer, without departing from the scope of the present invention.

Figure 2:
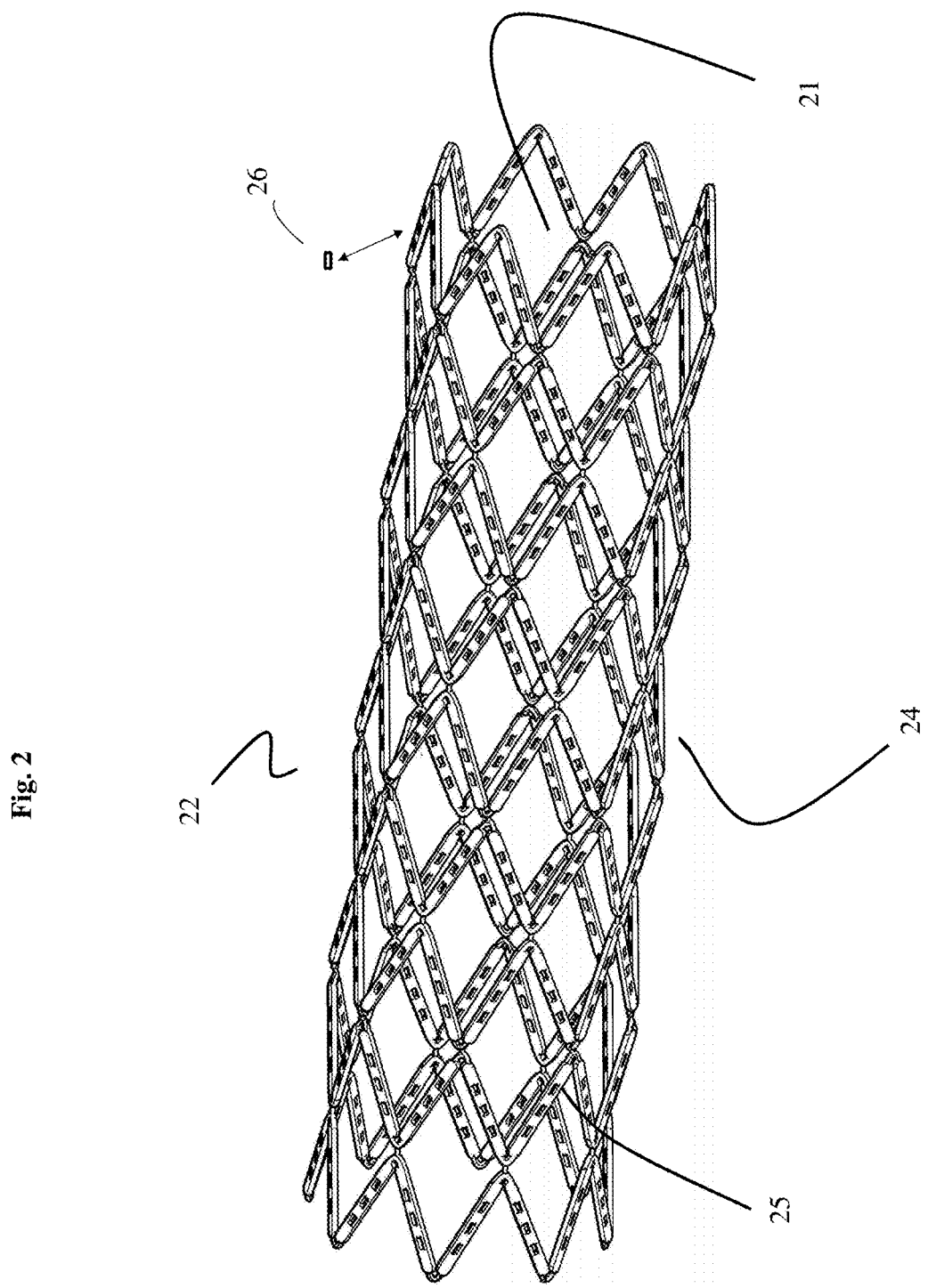
FIG. 2 is a top perspective of the stent according to an aspect of the invention.
Figure 3A:
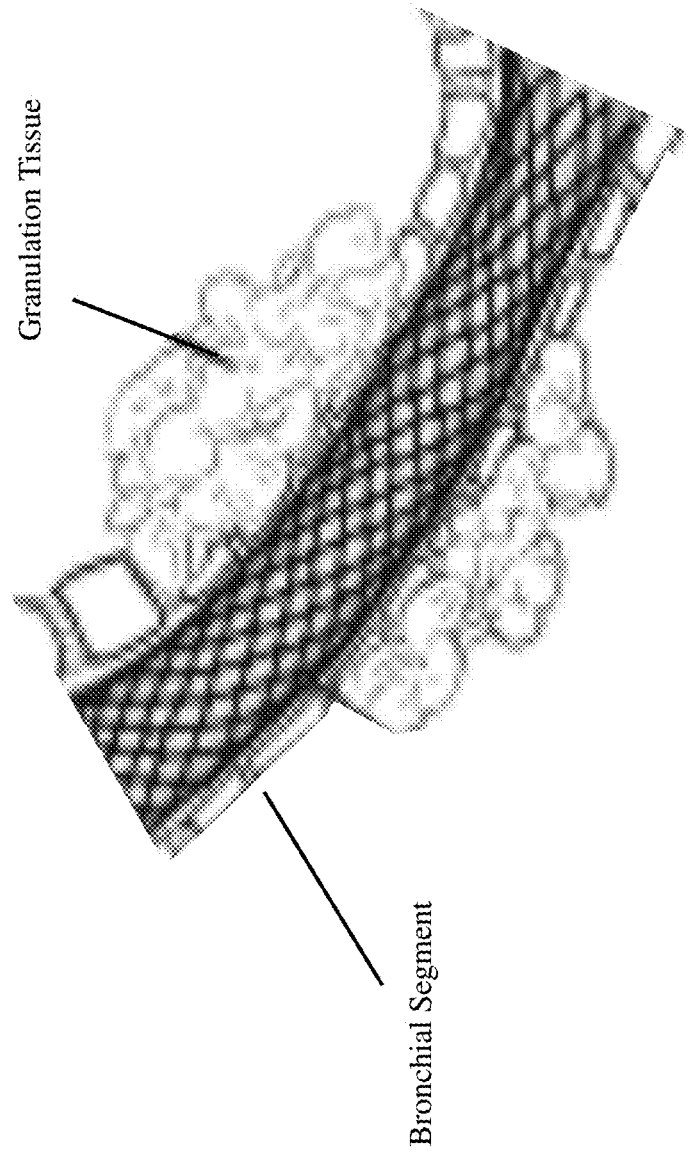
FIG. 3A depicts a stent implanted in a bronchial segment according to an aspect of the invention.
Figure 3B:
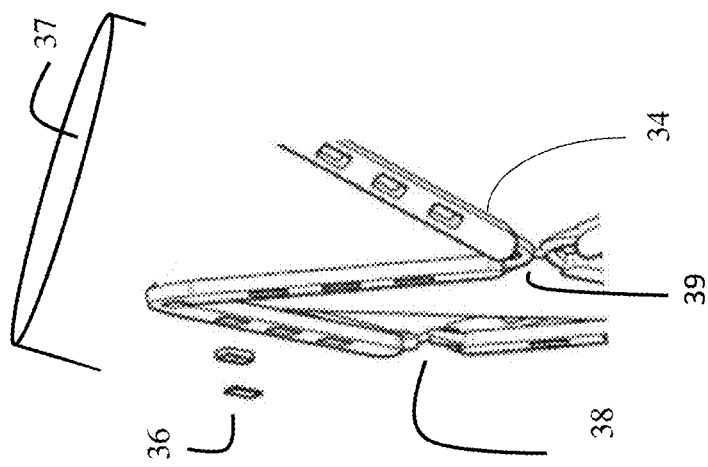
FIG. 3B is a fragmentary sectional view of a terminal segment of the bronchial implanted stent from FIG. 3A.
Figure 4:
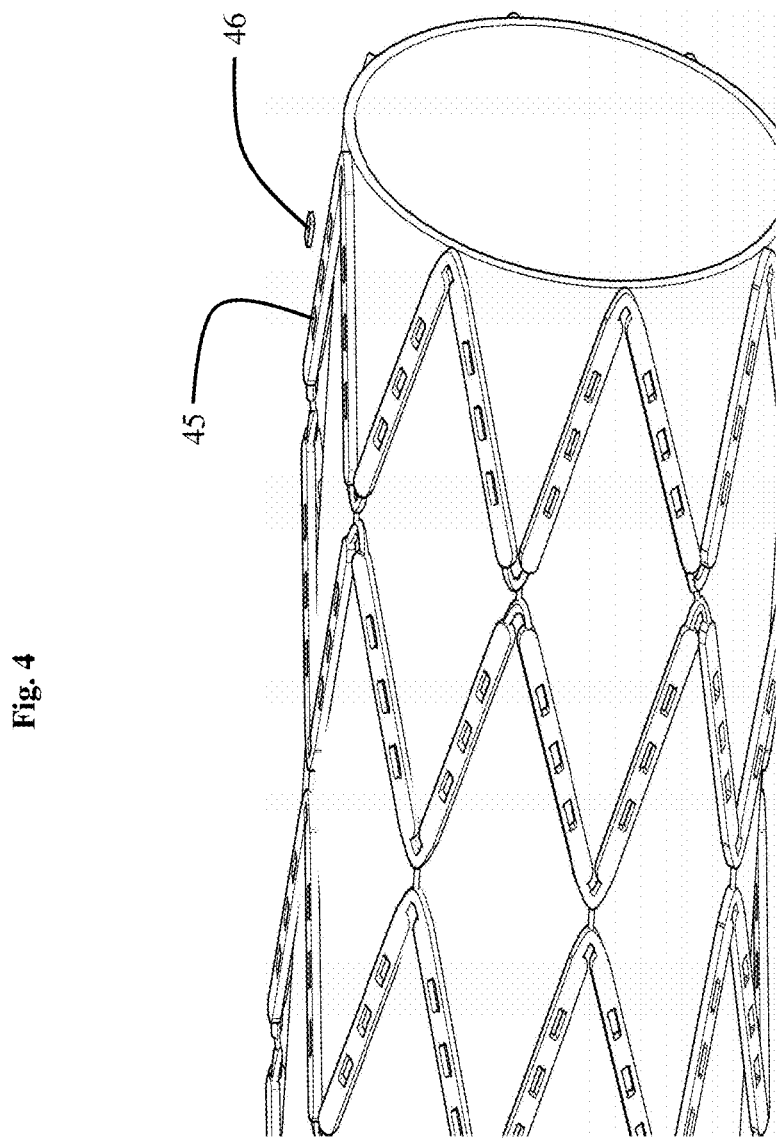
FIG. 4 depicts a close-up view of the capped and un-capped enclosure or reservoir in accordance with an aspect of the invention.
Figure 5:
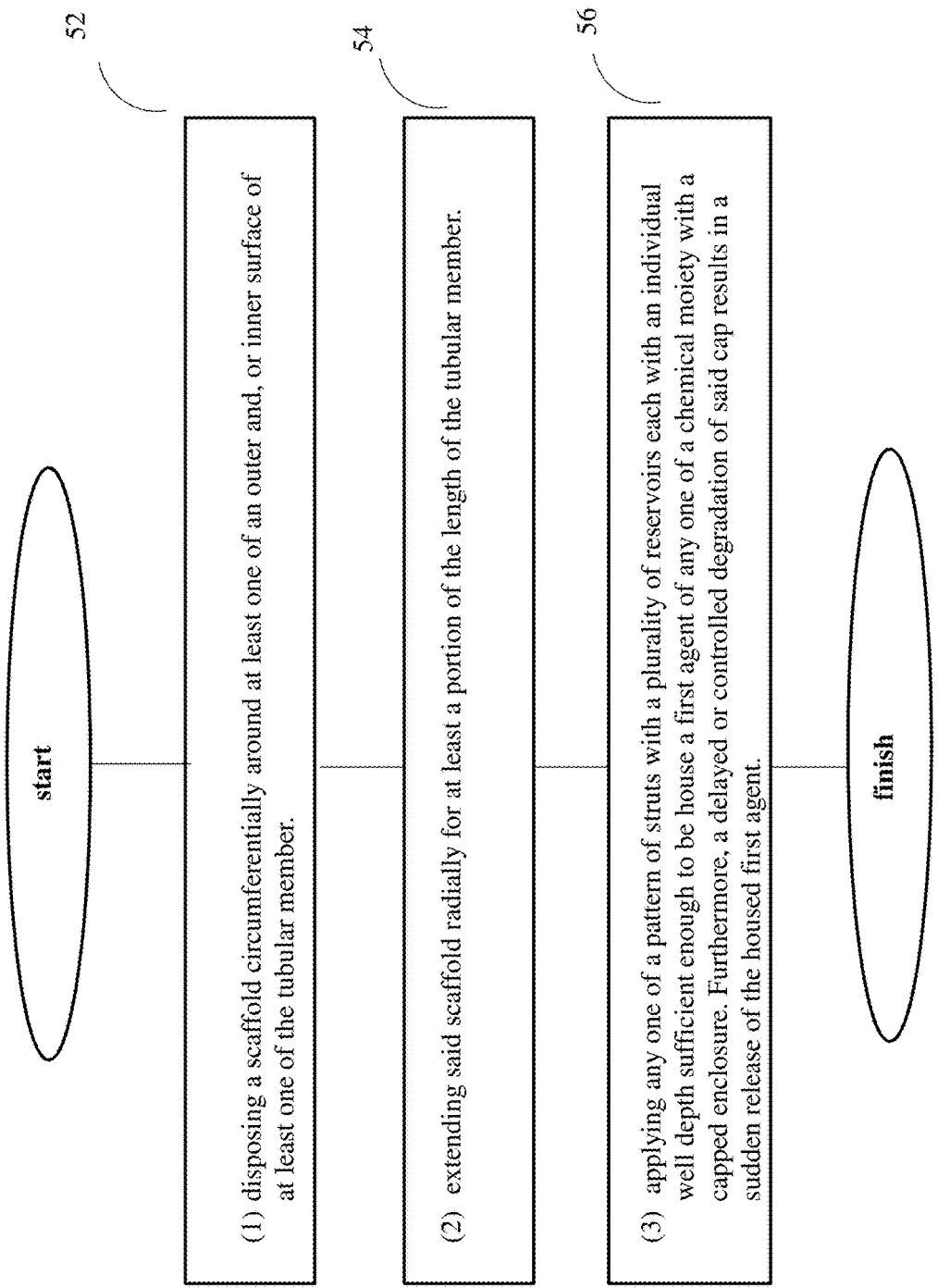
FIG. 5 is a method flow diagram illustrating the capped-release mechanism in accordance with an aspect of the invention.
Figure 6:
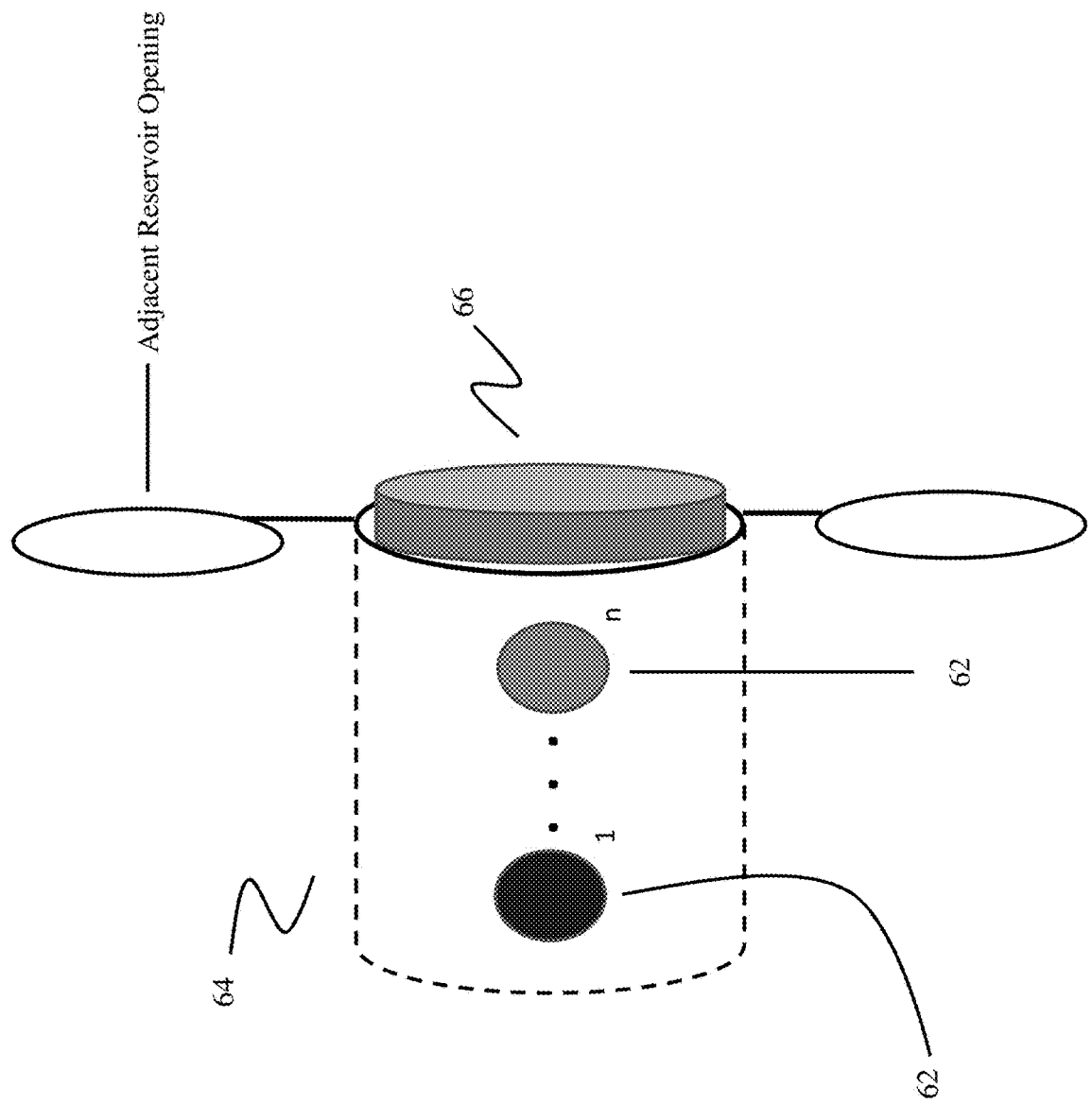
FIG. 6 illustrates a schematic of the capped-release mechanism on the abluminal surface in accordance with an aspect of the invention.
Figure 7:
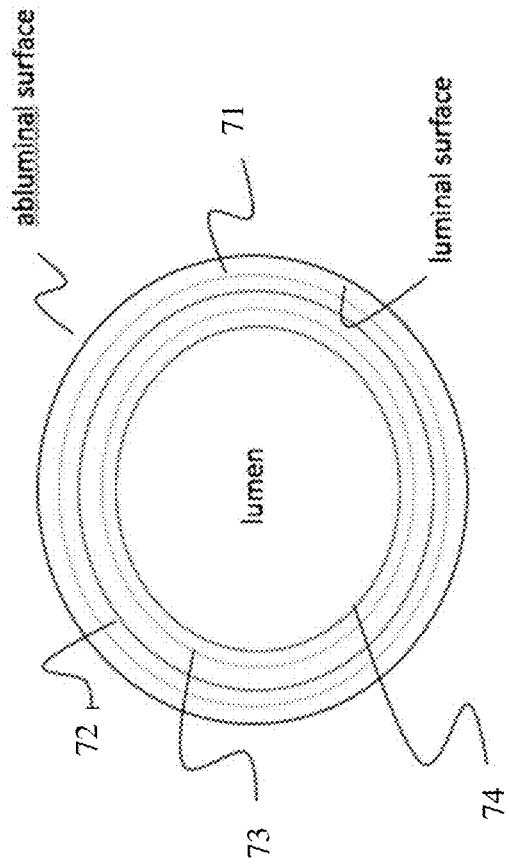
FIG. 7 illustrates a schematic of the multi-layered configuration of bioabsorbal layer and anti-mucosal layer on the luminal surface in accordance with an aspect of the invention.
Figure 8:
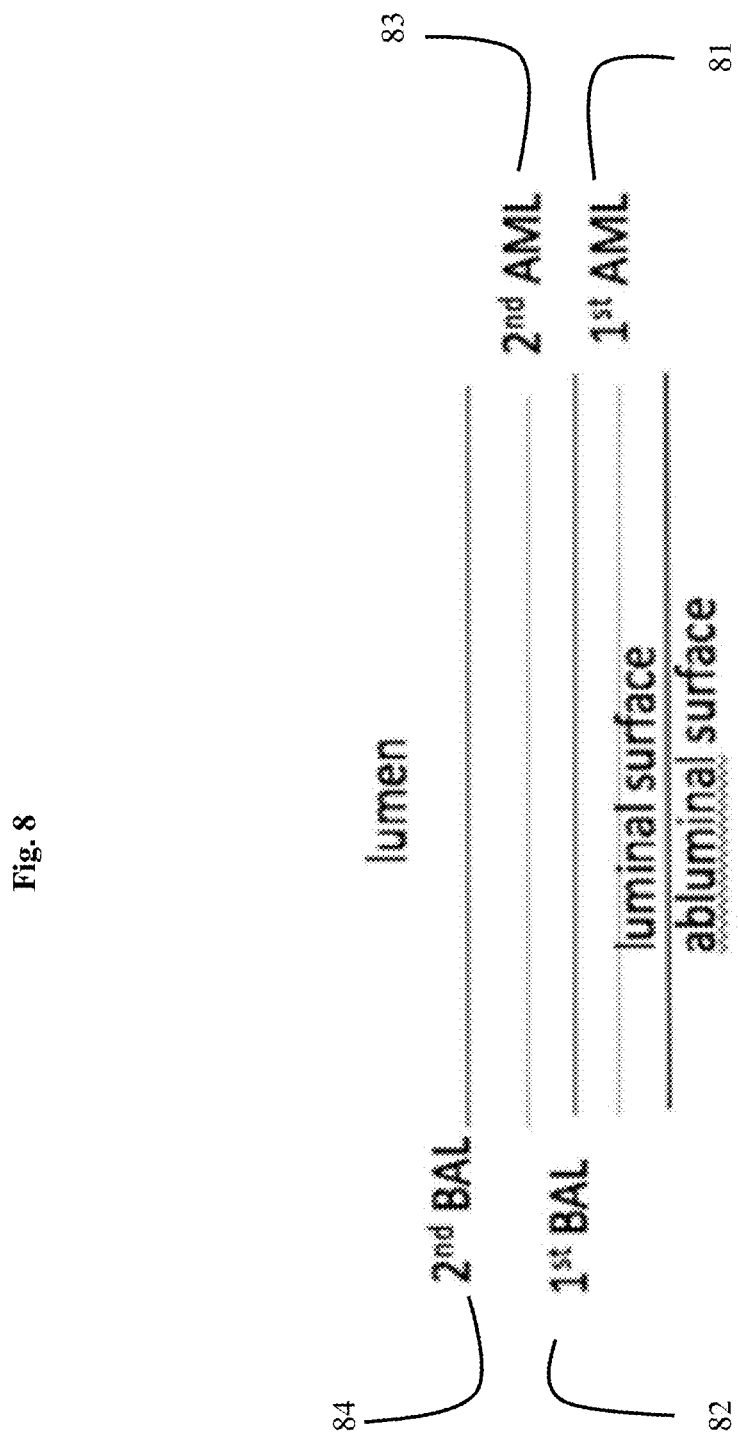
FIG. 8 illustrates a schematic of the multi-layered configuration of the luminal surface in accordance with an aspect of the invention.

FIGS. 1-7 illustrate various perspectives in accordance with exemplary aspects of the invention. The invention provides for an apparatus and method for a capped-release of agents: controlled, yet sudden release of an anti-granulation agent housed in a cap enclosure on at least one of the luminal, abluminal, and proximal or distal openings of the stent. Capped release referring to the controlled degradation of the cap, resulting in a sudden release of anti-granulation agents. The controlled degradation and sudden release mechanism results in a released agent with a higher therapeutic payload. FIGS. 1 and 2 are a top perspective of a capped-release stent according to an aspect of the invention. FIGS. 3A and 3B depict the stent implanted in a bronchial segment according to an aspect of the invention. FIG. 4 depicts a close-up view of the capped and un-capped enclosure or reservoir in accordance with an aspect of the invention. FIG. 5 is a method flow diagram illustrating the capped-release mechanism in accordance with an aspect of the invention. FIG. 6 illustrates a schematic of the capped-release mechanism on the abluminal surface in accordance with an aspect of the invention. FIG. 7 illustrates a schematic of the multi-layered configuration of bioabsorbal layer and anti-mucosal layer on the luminal surface in accordance with an aspect of the invention. Finally, FIG. 8 is a schematic of the multi-layered configuration of the luminal surface depicted in a horizontal fashion. It should be appreciated by a person of ordinary skill in the art that the figures and accompanying description depict only some embodiments of the invention, and should not be taken as limiting its scope.

In the case of a pulmonary or tracheobronchial stent, the unique ability of the scaffold and its corresponding agent is to disrupt the development of granulation tissue that accumulates at the peripheral edges of the stent which is a known cause of stent occlusion and therefore failure. The scaffolding and its corresponding agent is also unique in its ability to prevent another common problem, which is mucus inspissation and secretion build-up that forms within the lumen of the stent through timed, yet rapid release of agent or agents designed to prevent such occlusion. In the case of vascular stents, in either the central (cardiac/coronary and the great vessels) or peripheral vascular system (arteries and veins), occlusion develops due to the accumulation of inflammatory cells and smooth muscle, fibrous tissue, sometimes manifested by in situ thrombosis. A common scenario exemplifying this, is atherosclerosis, which in the coronary system is often managed by coronary stents. Stent occlusion and in situ thrombosis is a common, feared complication of cardiac stent placement. While strategies for prevention are include mTOR inhibitor and taxane based drug eluting capabilities of the stent, stent occlusion remains a major complication, thus there remains a need for optimizing their ability to p occlusions.

FIGS. 1 and 2 illustrate a top perspective of a stent in accordance with an aspect of the invention. FIG. 1 illustrates a top perspective of a stent with a strut configuration with open reservoirs, while FIG. 2 illustrates the same perspective with a strut configuration with capped reservoirs or enclosures. In a preferred embodiment, as illustrated in FIGS. 1 and 2, a stent apparatus may comprise: at least one lumen 11, 21 fittingly disposed within a tubular member 12, 22; a scaffold circumferentially disposed around at least one of an outer and, or inner surface of at least one of the tubular member 12, 22; said scaffold radially extending for at least a portion of the length of the tubular member 12, 22; said scaffold comprised of any one of a pattern of struts 14, 24 with a plurality of reservoirs 15, 25, each with an individual well depth sufficient enough to be house a first agent of any one of a chemical moiety with a capped 26 enclosure. Furthermore, a delayed or controlled degradation of said cap 26 results in a sudden release of the housed first agent. The sudden release of the first agent in this single agent-single cap reservoir configuration effectuates a prevention of a local recurrence of a tumor, granulation tissue, or fibrin sheath.

In another aspect of the invention, while not shown in FIG. 1 or 2, the scaffold may radially extend for at least a portion of the length of the tubular member 12, 22 and may be comprised of any one of a pattern of struts 14, 24 with a plurality of reservoirs 15, 25 with an individual well depth sufficient enough to be house more than one agent of any one of a chemical moiety within a capped 26 enclosure. Furthermore, a delayed or controlled degradation of said cap 26 results in a sudden release of the multiple agents. According to this multi-agent, single cap reservoir configuration, the sudden release of the first agent effectuates a prevention of a local recurrence of a tumor, granulation tissue, or fibrin sheath, while the at least second agent combats at least one of a build up of mucus or inflammation. In other embodiments, the at least second agent housed within the single-cap enclosure may have any type of therapeutic value.

While also not shown in FIG. 1 or 2, the reservoirs 15, 25 may have an individual well depth sufficient enough to house at least one agent within at least one cap 26 in a multi-cap reservoir configuration. In such an embodiment, the at least one agent in each cap enclosure of the multi-cap configuration may be of any one of a chemical moiety. Furthermore, a delayed or controlled degradation of each cap 26 may result in a sudden release of the housed multiple agents.

Now in reference to FIGS. 3A and 3B. FIG. 3A depicts a stent implanted in a bronchial segment according to an aspect of the invention. FIG. 3B is a fragmentary sectional view of a terminal segment of the bronchial implanted stent from FIG. 3A. As shown in FIG. 3A, the stent implanted in the bronchial segment is "open", meaning open space exists between the peak-and-valley" configuration of struts 34 (shown in the close-up of the terminal segment in FIG. 3B). This may allow for an increased potential to expand and contract in a body lumen—a bronchial segment 37 as depicted in FIG. 3B. In a preferred embodiment, stents should be very flexible in order to expand or constrict, while possessing enough radial strength to resist external compressive forces. The design and composition of the stent must allow for the stent to withstand constant radial pressure in order to maintain patency. The stents may possess an interlocking strut 34 configuration or valley-peak configuration to facilitate more effective agent delivery; prevent stent migration; and withstand greater radial pressure. In a preferred embodiment, a bridging element 38 connects one circumferential ring to another (above or below). Such a bridging element 38 provides for increased radial tensile strength to account for radial expansion and contraction Ductile hinges 39 form the intersection points in the peak-valley strut configuration. Such a ductile binge 39 allows for longitudinal expansion and to better withstand contractile forces.

While not shown in FIG. 3, a stent sleeve may comprise: at least one sleeve configured to be fittingly disposed over a tubular member portion of a stent; a scaffold circumferentially disposed around at least one of an outer surface of at the sleeve; said scaffold radially extending for at least a portion of the length of the sleeve; said scaffold comprised of any one of a pattern of struts with an individual reservoir disposed therebetween, each reservoir with a depth sufficient enough to be house a first agent of any one of a chemical moiety with a capped enclosure. Furthermore, a delayed degradation of said cap resulting in a sudden release of the at least one the housed first agent.

The sleeve may have the additional or off-label benefit of anchoring the stent better in the bronchial or vascular segment. The polymer based or non-polymer based sleeve may match the mounted c/s in at least one of color, strut geometry, composition, and size. Other embodiments call for a c/s sleeve that only matches the mounted c/s in terms of size and dimension. Such a sleeve embodiment may be structurally and functionally equivalent to the open stent configuration depicted in FIG. 3A or 3B.

While also not shown in FIG. 3A or 3B, the cap may have a spherical or hemi-spherical configuration. Such a configuration may be more conducive to a controlled degradation of the bioabsorbal layer. The cap may have any one of a configuration, such as a flat, concave, or a steeple configuration. Each specific configuration may confer a different degradation rate of the cap, thereby releasing the anti-granulation agent suddenly after the timed degradation of the cap. Various applications may call for varying rates of degradation and a sudden release of anti-granulation agents depending on the dwelled environment. Furthermore, any number of strut geometries or configurations may be adopted for the scaffold of the c/s or sleeve.

FIG. 4 depicts a close-up view of the capped and uncapped enclosure or reservoir in accordance with an aspect of the invention. The reservoirs 45 proximal to port openings may have a higher payload and, or the cap 46 on reservoirs 45 proximal to port openings may have a faster degradation rate—in order to account for the port openings propensity for increased granulation tissue build up. The port openings may also have an edge reinforcement to further stave off the increased accumulation of granulation tissue, mucus, or secretory incrustation.

In continuing reference to FIG. 4, to overcome some of the potential drawbacks of metal stents, several companies are pursuing the development of bioresorbable or bioabsorbable stents. Like metal stents, placement of a bioresorbable stent will restore blood flow and support the vessel through the healing process. However, in the case of a bioresorbable stent, the stent will gradually resorb and be benignly cleared from the body, leaving no permanent implant. In the case of bioabsorbal stents, the vast majority are polymer-based stents that break down over time into lactic acid.

As shown in FIG. 4, the degradable portion, bioabsorbal portion, or bioresorbal portion are relegated exclusively to the capped portion 46 anterior to each reservoir 45. The advantage is that each reservoir 45 can be selectively tuned for degradation rates for controlled release of housed agents. For instance, one reservoir 45 may have a bioabsorbal or bioresorbal cap 46 of one rate, while the adjacent reservoir has a cap 46 of another rate. This differential may allow for zoning the capped-release of agents based on what portions of the stent are prone to build up. In addition to the port openings being exceptionally prone to build-up, other portions of the tubular member may be prone due to interaction with the patients venous/airway anatomy.

While standard drug-eluting stents delivering adjunctive pharmacological intervention do lower incidence rates of restenosis, there are a number of other complications that arise from standard drug-elution stents known in the art: Most notably inflammation or thrombosis. In the cardiac application, stent thrombosis (ST) is the occlusion of a stented coronary artery due to thrombus formation. ST risks include death in 20-48% or major myocardial infarction (MI) in 60-70% of the cases. In the context of pulmonary applications, mitomycin C and sirolimus have lowered incidence rates of granuloma tissue formation. However, other clinical outcomes may be at risk of occurring as a result of standard drug-elution stent modalities, such as pulmonary thrombus embolism (PTE). It is believed that the use of durable polymer or foreign metals is attributable to the increased inflammation risk of long-dwelling stents. Newer generation of stents have introduced polymer-free stents, along with bioresorbal scaffolding, but reviews are mixed. Inflammation is still a pervasive issue related to long-dwelling stents, both in the pulmonary or coronary context.

It is believed that the blanket coating of the bioresorbal, bioabsorbal, or biodegradable layer embedded with any number of agents throughout the surface of the stent elicits the initial acute inflammatory cell response within the first week of dwelling. Additionally, inflammation is particularly severe around stent struts, presumably due to the trauma to the vessel wall caused by the protrusion of the struts. The blanket surface coating of the bioresorbal material with embedded agents and strut protrusion activates inflammatory cells, with early neutrophil recruitment to the exposure site, followed by prolonged macrophage accumulation. After a month, a chronic inflammatory response is activated: proliferation of smooth muscle cells, fibrin, and granulation tissue. Beyond 30 days, fibrin and chronic inflammation persist, and smooth muscle cells and extracellular matrix (proteoglycans and collagen) further enrich the expanding neointima.

As demonstrated in FIG. 4, the claimed invention limits the bioresorbal material to the cap structures 46, and are not blanketed across the surface of the stent. This capped configuration greatly limits the surface area of the bioresorbal material, thereby reducing the inflammation risks. Moreover, the scaffold struts and resulting reservoirs 45 may be configured to mitigate the risks of vessel trauma, thereby reducing inflammation risks. The scaffolding struts and resulting reservoirs 45 may have a distinct shape, design, and dimension to further mitigate inflammation risks. As shown in FIG. 4, the strut design is one of a circumferential ring of a peak-and-valley configuration, wherein each peak and valley is connected via a ductile hinge 49 and each ring is connected to the above and below ring via a bridge element 48. Moreover, the reservoir 45 and strut profile illustrated in FIG. 4 may be interpreted as being smaller than the standard drug-eluting stent strut/reservoir, thereby reducing the risk of trauma and subsequent inflammation.

In continuing reference to FIG. 4, the bioabsorbal, bioresorbal, or biodegradable material comprising the caps 46 may be any one of, or combination of, polyglycolic acid (PGA), polyactic acid (PLA), and, or co-polymers, self reinforcing. Housed within the reservoirs 45 and enclosed under the cap 46, are agents 49 that may be any one of, or combination of, statins, corticosteroids, antiplatelets, immunosuppressives, anti-cancer drugs, mitomycin C, sirolimus, anti-proliferatives, anti-granulation, anti-fibrin, anthrombogenic-activating, NF-kB inhibiting, and, or any agent with any one of a therapeutic value. Paclitaxal or an mTOR (mammalian target of rapamycin) inhibitor, such as sirolimus, may be used as well. Zotarolimus, everolimus and biolimus are sirilimus analogs that may be used as agents as well.

Though not shown in FIG. 4, the reservoir/s may not just be the well-like structures disposed within the struts, as described in earlier embodiments. In some embodiments, the reservoir may be all or a portion of the space outside of the strut geometry (inter-strut space). In this embodiment, the strut profiles serve as the reservoir wall or edges, wherein the at least one agent is housed within this space and is enclosed by a bioabsorbal, bioresorbal, or biodegradable cap for a controlled release of the agent. The cap plane may be at level with the height of any one of the strut walls to form a contiguous surface layer. Alternatively, the cap plane may be at a slightly lower level than the height of any one of the strut walls—allowing for the struts to still maximize traction and mitigate stent migration. Differential agent loading or cap degradation rates may still be achieved, wherein zoning is done based on strut geometry, vascular/bronchial segment interaction, or tubular regions prone to tissue build-up.

Also not depicted in FIG. 4 is a reservoir system that occupies the top circumferential layer of the abluminal surface, spanning at least a portion of the length of the stent. For instance, the top layer may be directly adjoining the top wall of the tubular member and configured for housing any number or dosage of agents. This reservoir configuration may have a circumferential cap layer that spans a portion or the entire length of the stent. Another reservoir configuration may call for a strut configuration with distinct geometry and profile, that doubles as an additional or tiered cap for controlled release of the agents. In such a reservoir configuration, the inter-strut space may be configured with a degrading cap enclosing an agent-laden reservoir—or be completely reservoir and cap-free. Once again, differential agent loading or cap degradation rates may still be achieved, wherein zoning is done based on strut geometry, vascular/bronchial segment interaction, or tubular regions prone to tissue build-up.

FIG. 5 represents a method flow of the capped-release mechanism (CRM) in accordance with an aspect of the invention: (1) disposing a scaffold circumferentially around at least one of an outer and, or inner surface of at least one of the tubular member 52; (2) extending said scaffold radially for at least a portion of the length of the tubular member 54; and (3) applying any one of a pattern of struts with a plurality of reservoirs each with an individual well depth sufficient enough to be house a first agent of any one of a chemical moiety with a capped enclosure. Furthermore, a delayed or controlled degradation of said cap results in a sudden release of the housed first agent 56. The sudden release of the first agent in this single agent-single cap reservoir configuration effectuates a prevention of a local recurrence of a tumor, granulation tissue, or fibrin sheath. Any number of agents within any number of a capped enclosure may be possible without departing from the scope of the invention. The delivery system may be a flexible or rigid bronchoscopy. Radiopaque markers may be utilized for targeted deployment and tracking of stent after deployment.

FIG. 6 illustrates a high-level schematic depicting the configuration of the capped-release mechanism on the abluminal surface of the c/s. As shown, a single agent 62 may be housed within a single cap-layered reservoir 64. In other embodiments, while not shown, a matrix of different agents 62 may be within each reservoir 64. The cap 66 may biodegrade, resulting in a release or exposure of the agent/s 62 on the abluminal surface to target against phenomena, such as, the development of granulation tissues or in growth of tumors that would cause intraluminal obstruction.

In certain embodiments, the reservoir 64 walls themselves biodegrade, resulting in the release of the agent/s 62. In such an embodiment, the agent/s 62 may be embedded within or behind the reservoir 64 walls, not requiring a separate cap 66 feature. Much like the cap 66 of the capped configuration, the reservoir 64 wall may also have varying thicknesses in order to degrade with differential timing to expose or release agents 62 depending on any one of a tissue/tumor growth cycle, stent structural features, and body lumen environment. In other embodiments, the abluminal surface of the stent may have hemi-spherical protrusions—each serving as a top wall of a reservoir 64 or a cap 66 feature adjoining the surface of the stent without a reservoir 64 feature—enclosing the at least one agent 62 for release upon controlled degradation.

In other embodiments, the reservoir 64 wall or cap 66 may be largely based on at least one of a bioabsorbal, bioresorbal, or biodegradable composition, in which certain functional groups in the chemical structure are varied between reservoirs 64 or stent segments. This variation in the chemical structure would enable the differential timing of agent 62 release. In this scenario, the thickness of reservoir 64 walls or the cap 66 may be uniform.

Other potential points of variation to confer differential agent release may be any one of, or combination of, a distribution of repeat units in multimers; ionic groups; overall structure; molecular-weight distribution; morphology (amorphous/semicrystalline, microstructures, residual stresses); co-polymers with certain hydrophilic/hydrophobic interactions; hydrogen or ionic bonding; dendrimers or star polymers as nanoparticles for immobilization of enzymes, drugs, peptides, or other biological agents; and hydrocolloids and carbohydrate-based polymers.

The release of the active agent may be constant, cyclic or triggered. The purpose is to achieve more effective delivery; eliminating both under and overdosing; maintenance of drug levels within a desired range; fewer administrations; optimal use of the drug; and increased patient compliance. Providing capped-release control over the drug delivery can be the most important factor at times when traditional oral or injectable drug formulations cannot be used. These include situations requiring the slow release of water-soluble drugs, the fast release of low-solubility drugs, drug delivery to specific sites, drug delivery using nano-particulate systems, delivery of two or more agents with the same formulation, and systems based on carriers that can dissolve or degrade and be readily eliminated.

FIG. 7 illustrates a high-level schematic depicting the configuration of the anti-mucosal and bioabsorbal layers on the luminal surface of the c/s. The multi-layered luminal configuration allows for a staged-release of an anti-mucosal. The first stage is released immediately activating a prophylactic against the initial deposits of a mucosal or any other encrustation within the stent lumen. After a set time, the second stage activates a booster response against the long-term build up of a mucosal or any other encrustation within the stent lumen.

In reference to FIG. 7, a preferred embodiment of the luminal surface and multi-layer configuration of anti-mucosal and bioabsorbal layers are shown. FIG. 8 depicts the layering in a horizontal fashion to further illustrate the interrelation of bioabsorbal layers and anti-mucosal layers. As shown, the staged luminal release is accomplished by: a first anti mucosal layer 71, 81 coating on a luminal layer of a stent; a first bioabsorbal layer 72, 82 with a specific degradation rate coupled to the first anti mucosal layer 71, 81; at least one other anti mucosal layer 73, 83 coupled to the first bioabsorbal layer 72, 82; at least one other bioabsorbal layer 74, 84 with a different degradation rate from the first bioabsorbal layer 72, 82 and coupled to the at least one other anti mucosal layer 73, 83 and exposed to a stent lumen; and wherein the at least one other bioabsorbal layer 74, 84 degrades immediately upon stenting to release the at least one other anti mucosal layer 73, 83 immediately as a prophylactic, and a delayed degradation of the first bioabsorbal layer 72, 82 resulting in a delayed release of the first anti mucosal layer 71, 81 as a booster anti mucosal response.

The terms and phrases as indicated in quotation marks (" ") in this section are intended to have the meaning ascribed to them in this Terminology section applied to them throughout this document, including in the claims, unless clearly indicated otherwise in context. Further, as applicable, the stated definitions are to apply, regardless of the word or phrase's case, tense or any singular or plural variations of the defined word or phrase.

The term "or" as used in this specification and the appended claims is not meant to be exclusive rather the term is inclusive meaning "either or both".

References in the specification to "one embodiment", "an embodiment", "a preferred embodiment", "an alternative embodiment", "a variation", "one variation", and similar phrases mean that a particular feature, structure, or characteristic described in connection with the embodiment is included in at least an embodiment of the invention. The appearances of phrases like "in one embodiment", "in an embodiment", or "in a variation" in various places in the specification are not necessarily all meant to refer to the same embodiment or variation.

The term "couple", "coupled", "coupling", or any variation thereof, as used in this specification and the appended claims refers to either an indirect or direct connection between the identified elements, components or objects. Often the manner of the coupling will be related specifically to the manner in which the two coupled elements interact.

We claim:
1. An apparatus comprising:
    at least one lumen fittingly disposed within a tubular member;
    a scaffold circumferentially disposed around at least one of an outer surface of at least the tubular member;
    said scaffold radially extending for at least a portion of the length of the at least tubular member;
    said scaffold comprised of any one of a pattern of interlocking struts with individual well-like reservoirs disposed; and
    each reservoir [having a depth sufficient enough to house] housing a plurality of capped enclosures, said capped enclosures with at least a first an agent of any one of a chemical moiety, each of the enclosures capped with a cap of a different degradation rate resulting in a staged degradation of the caps and release of agents within the same reservoir.

2. The apparatus of claim 1, wherein the at least first agent released effectuates a prevention of a local occurrence or recurrence of a stent occluding tissue.

3. The apparatus of claim 1, further comprising at least a second agent released with at least one of a stent occlusion prevention value or a therapeutic value.

4. The apparatus of claim 1, wherein a body lumen for stent implantation and dwelling may be at least one of a cardio-vascular or tracheal-bronchial.

5. The apparatus of claim 1, wherein the reservoir may have at least one agent, each agent of any dosage or concentration, enclosed within a single cap that may either degrade, bioabsorb, or bioresorb to release the at least one agent.

6. The apparatus of claim 1, wherein the reservoir may have a plurality of caps with varying degradation rates, each enclosing at least one agent with a unique value, and the degradation of each cap stage releasing each agent with a unique value.

7. The apparatus of claim 1, wherein the interlocking pattern of struts is a 'peak-and-valley' strut configuration.

8. The apparatus of claim 7, wherein the 'peak-and-valley' strut configuration connects one circumferential ring with another via a bridging element, and wherein at least one of a peak or valley within each ring is interposed with a ductile hinge.

9. The apparatus of claim 1, wherein the reservoirs are disposed on the inter-strut space along the tubular surface of the stent.

10. The apparatus of claim 9, wherein the at least one inter-strut reservoir is one collective reservoir defined by a strut geometry and fittingly enclosed by the cap.

11. The apparatus of claim 10, wherein the fittingly enclosed cap for the collective inter-strut reservoir is planar with the height of a wall of the struts, thereby forming a contiguous layer.

12. The apparatus of claim 10, wherein the fittingly enclosed cap for the collective inter-strut reservoir is lower than the height of a wall of the struts, thereby allowing the struts to maintain traction with a body lumen wall to prevent stent migration.

13. The apparatus of claim 9, further comprising reservoirs on the strut in addition to the inter-strut space.

14. The apparatus of claim 1, wherein an entire circumferential layer that extends at least a portion span of the stent is one collective reservoir enclosed by the collective cap.

15. The apparatus of claim 1, wherein the caps may vary degradation rates by reconfiguring the structure of the cap between at any one of a steepled, hemi-spherical, spherical, flat, concave, convex.

16. The apparatus of claim 1, wherein the cap may vary degradation rates by reconfiguring the chemical structure of the cap.

17. The apparatus of claim 16, wherein the chemical structure reconfigured is at least one of a functional group.

18. The apparatus of claim 1, further comprising zones of differential agent loading or cap degradation rates based on at least one of a strut geometry, vascular/bronchial segment interaction, or tubular regions prone to tissue build-up.

19. A stent sleeve apparatus comprising
at least one sleeve fittingly disposed over and under a tubular member portion of a stent;
a scaffold circumferentially disposed around at least one of an outer and inner surface of the sleeve;
said sleeve radially extending for at least a portion of the length of the tubular member portion of the stent;
said scaffold comprised of any one of a pattern of interlocking struts with individual wells therebetween;
each well [having a depth sufficient enough to house] housing at least a first agent of any one of a chemical moiety, each of the wells capped to form an enclosure;
wherein a delayed degradation of said cap results in a sudden release of the housed at least first agent; and
said first agent effectuating a prevention of a local recurrence of a tumor or granulation tissue.

20. The apparatus of claim 19, wherein the sleeve is open, wherein the inter-strut space is empty.

21. The apparatus of claim 19, wherein the sleeve is closed, wherein the inter-strut space is filled with a top surface of a tubular member encircling to form a stent lumen, said surface comprised of at least one of a polymer and non-polymer composition.

* * * * *